US006462219B2

(12) United States Patent
Burdet et al.

(10) Patent No.: US 6,462,219 B2
(45) Date of Patent: Oct. 8, 2002

(54) PROCESS FOR PRODUCING 3-HYDROXYPROPIONITRILE

(75) Inventors: Bruno Burdet, Baldersheim (FR); August Ruettimann, Arlesheim (CH); Johann Riegl, *deceased*, late of Bad-Krozingen (DE), by Karin Riegl, legal representative; *by Thomas Andreas Riegl, legal representative*, Teningen (DE); by Maximilian Lutz Riegl, legal representative, Bad Krozingen (DE)

(73) Assignee: Roche Vitamins, Inc., Parsippany, NJ (US)

( * ) Notice: Subject to any disclaimer, the term of this patent is extended or adjusted under 35 U.S.C. 154(b) by 0 days.

(21) Appl. No.: 09/764,549

(22) Filed: Jan. 17, 2001

(65) Prior Publication Data

US 2002/0040163 A1 Apr. 4, 2002

(30) Foreign Application Priority Data

Jan. 25, 2000 (CH) ................................................ 0144/00

(51) Int. Cl.[7] .......................................... C07C 255/00
(52) U.S. Cl. ..................................................... 558/451
(58) Field of Search ......................................... 558/451

(56) References Cited

FOREIGN PATENT DOCUMENTS

| DE | 2655794 | 2/1985 |
| JP | 58-185550 | 10/1983 |
| JP | 64-90160 | 4/1989 |
| JP | 1-160949 | 6/1989 |

OTHER PUBLICATIONS

English translation of Konstantinov, et al., "A New Method for the Preparation of 2–Cyanoethanol," *J. Org. Chem. of the USSR*, vol. 28, No. 6, pp. 1087–1088 (1987).
Partial English language translation of JP 196,850 (1984).
Derwent English language abstract of DE 2655794 (document B1 above) 1978.
Derwent English language abstract of JP 1–160949 (document B2 above) 1989.
Derwent English language abstract of JP 58–185550 (document B3 above) 1983.
English translation of JP 64–90160 (document B4 above) 1989.

*Primary Examiner*—Joseph McKane
*Assistant Examiner*—Joseph Murray
(74) *Attorney, Agent, or Firm*—Bryan Cave, LLP

(57) ABSTRACT

A process for the production of 3-hydroxypropionitrile is provided. This process includes (a) reacting acrylonitrile with water at a defined molar ratio in the presence of a weak base under specific temperature and pressure conditions until a conversion in the range of about 40% to about 80% has been achieved; (b) after cooling the mixture obtained in (a), separating off its aqueous phase; (c) distilling off the acrylonitrile from the organic phase remaining after (b); (d) subjecting the mixture obtained in (c) to pyrolysis at specific temperature and pressure conditions in the presence of a basic catalyst to obtain a mixture consisting mainly of 3-hydroxypropionitrile and acrylonitrile; and (e) isolating the desired 3-hydroxypropionitrile by fractional distillation from the mixture obtained in (d). Such a process in which the basic aqueous phase and the acrylonitrile that has been distilled off are recycled represents a preferred embodiment.

17 Claims, No Drawings

PROCESS FOR PRODUCING 3-HYDROXYPROPIONITRILE

FIELD OF THE INVENTION

The present invention is concerned with a process for the production of 3-hydroxypropionitrile, which is an important intermediate in the process for the manufacture of panthenol. The end product, especially its d(+) isomer, is a valuable agent for the treatment of dermatoses, burns and infectious ulcers, as well as a valuable additive in shampoos and other cosmetics.

BACKGROUND OF THE INVENTION

Various methods for the production of 3-hydroxypropionitrile are known from the literature. For example, the reaction of 2-chloroethanol with an alkali cyanide to yield 3-hydroxypropionitrile (also known as "ethylene cyanohydrin") was described in Annalen der Chemie und Pharmacie 128, 1 (1863). Later publications, such as, for example, Org. Synth. 3, 57 (1923), J. Soc. Chem. Ind. 67, 458 (1948) and Britton et al., U.S. Pat. No. 2,311,636, concern the optimization of this basic production method. Despite the high yields allegedly achieved, the process is uninteresting commercially because of the relatively high purchase price of the 2-chloroethanol starting material, as well as the difficulty in controlling the exothermic reaction. Moreover, not only is there contamination with salt but there is also great expense involved in isolating and purifying the product of the process.

The successful production of 3-hydroxypropionitrile by the addition of hydrocyanic acid to ethylene oxide was reported around 1930 in various German patents, namely in German Patents Nos. 561,397, 570,031 and 577,686. The optimization of this addition process was described in Luskin, U.S. Pat. No. 2,653,162, in which a carboxylic acid sodium salt resin is used as the weak base, water is used as the solvent, and the reaction is effected at 45–50° C. Still later disclosures of the production of 3-hydroxypropionitrile by the addition of hydrocyanic acid to ethylene oxide appear in German Offenlegungsschrift No. 4,304,002 as well as in Merger et al., U.S. Pat. No. 5,268,499. However, the two starting materials are very problematical with respect to toxicity and handling. Therefore, these processes would no longer be considered in developing an up-to-date production process for 3-hydroxypropionitrile.

The production of the known 1:1 addition product of water and acrylonitrile (i.e. of 3-hydroxypropionitrile) in the presence of a basic catalyst gives rise to certain difficulties since the product reacts with further acrylonitrile to give the condensation product bis(cyanoethyl)ether, $NC(CH_2)_2O(CH_2)_2CN$, as described in Howk et al., U.S. Pat. No. 2,579,580. Howsmon, U.S. Pat. No. 3,024,267 and Japanese Patent Publication (Kokai) No. 196,850/1984 disclose that somewhat better yields of the desired 3-hydroxypropionitrile are achieved when the reaction is carried out in a large excess of water (i.e. at high dilution) or according to J. Org. Chem. USSR 1987, 1087, in the presence of a large amount of base. However, these measures are uneconomical, especially because of the unavoidably complicated working up, the evaporation of water, and the contamination with salt. Moreover, at such high dilution, small to medium amounts of bis(cyanoethyl)ether are also formed.

The reaction of aqueous formaldehyde with acrylonitrile in the presence of strongly basic Amberlyst® IRA-400, OH⁻ form, at about 40° C. is proposed in German Patent No. 2,655,794 as a possible solution to the above problems. However, the indicated yield of 3-hydroxypropionitrile, 75%, is moderate in this case, too.

Thus, the processes outlined above for the direct production of 3-hydroxypropionitrile have evident disadvantages.

Japanese Patent Publications (Kokai; JP) Nos. 160,949/1989, 90,160/1989, and 185,550/1983 disclose that bis(cyanoethyl)ether can be produced from acrylonitrile and water in the presence of a strong basic ion exchanger, and that the product can subsequently be pyrolyzed by means of a basic catalyst to yield the desired 3-hydroxypropionitrile and acrylonitrile. The base-catalyzed production of bis(cyanoethyl)ether from acrylonitrile and water is also known from earlier references, such as, for example, Org. Reactions 5, 79 (1945) (review article), J.A.C.S. 65, 23 (1943), J.A.C.S. 67, 1996 (1945), Ind. Eng. Chem. 44, 1388 (1952), German Patents Nos. 731,708 and 1,189,975 as well as U.S. Pat. Nos. 2,382,036, 2,448,979 and 2,816,130 to Bruson, Hopff et al., and Selcer et al., respectively. As the catalyst for this 2:1 addition reaction, a strong base (e.g. sodium hydroxide) is generally used, although a strongly basic Amberlyst® catalyst, such as Amberlyst® IRA-400, OH⁻ form, can also be used. At least small amounts of 3-hydroxypropionitrile are formed irrespective of the acrylonitrile:water ratio, the reaction temperature, or the respective strong base that is used. Based on these documents, yields of up to about 77% could be achieved using strongly basic catalysts (e.g. Amberlyst® IRA-400, OH⁻ form). The cleavage of the bis(cyanoethyl)ether described in the aforementioned Japanese patent publications is effected using a basic catalyst, especially aqueous or aqueous-methanolic potassium hydroxide/dipotassium phosphate at 72–100° C./5 mm Hg, with about 85% yield (JP 160,949/1989, JP 90,160/1989) or tetraethylammonium acetate at 100–105° C./10 mm Hg, with about 86% yield (JP 185,550/1983).

SUMMARY OF THE INVENTION

One aspect of the claimed invention is a process for the production of 3-hydroxypropionitrile that includes the reaction of water with acrylonitrile to give a mixture of the desired product and the bis(cyanoethyl)ether condensation product, and then the pyrolysis of this product mixture to additional 3-hydroxypropionitrile, whereby not only the mentioned reaction, but also the pyrolysis, are carried out under specific base-catalyzed and other conditions. Another aspect of this process is that, if desired, unreacted reactants, especially acrylonitrile and the water containing the catalyst, can be conducted back into the reaction system for re-use. This overall multi-stage process provides for the altogether surprisingly economical production of 3-hydroxypropionitrile, particularly because this product is formed only to some extent during the first step of the process, yet is obtained in high yield after the penultimate (pyrolysis) step.

The claimed process includes (a) reacting acrylonitrile with water at a defined molar ratio in the presence of a weak base under specific temperature and pressure conditions until a conversion in the range of about 40% to about 80% has been achieved; (b) after cooling the mixture obtained in (a), separating off its aqueous phase; (c) distilling off the acrylonitrile from the organic phase remaining after (b); (d) subjecting the mixture obtained in (c) to pyrolysis at specific temperature and pressure conditions in the presence of a basic catalyst to obtain a mixture consisting mainly of 3-hydroxypropionitrile and acrylonitrile; and (e) isolating the desired 3-hydroxypropionitrile by fractional distillation from the mixture obtained in (d). Such a process in which the basic aqueous phase and the acrylonitrile that has been distilled off are recycled represents a preferred embodiment.

One embodiment of the invention is a process for producing 3-hydroxypropionitrile. This process includes (a) reacting acrylonitrile with water at a molar ratio of about 1:0.5 to about 1:20 in the presence of a weak base at a temperature of about 80° C. to about 150° C. and at a pressure of about 1 bar (0.1 MPa) to about 5 bar (0.5 MPa) to form a two-phase organic-aqueous mixture and until a conversion of the acrylonitrile and water to 3-hydroxypropionitrile of about 40% to about 80% is achieved, wherein the organic phase consists essentially of bis(cyanoethyl)ether, 3-hydroxypropionitrile and unreacted acrylonitrile, and the aqueous phase consists essentially of an aqueous solution of the weak base; (b) cooling the mixture obtained in (a) and separating the aqueous phase from the organic phase; (c) distilling off the acrylonitrile from the organic phase remaining after (b) to obtain a mixture consisting essentially of bis(cyanoethyl)ether and 3-hydroxypropionitrile; (d) heating the mixture obtained in (c) to a temperature of about 120° C. to about 160° C. at a pressure of about 5 mbar (0.5 kPa) to about 500 mbar (50 kPa) in the presence of a basic catalyst selected from the group consisting of calcium, magnesium, strontium, titanium, iron and zinc oxides, alkali metal acetates, alkali metal formates, alkali metal and barium carbonates, alkali metal bicarbonates, calcium and copper hydroxides, di- and trisodium phosphates, sodium fluoride, sodium silicate and high boiling trialkylamines, to form a mixture consisting essentially of 3-hydroxypropionitrile and acrylonitrile; and (e) isolating the 3-hydroxypropionitrile by fractional distillation from the mixture obtained in (d).

Another embodiment of the invention is a process for the production of 3-hydroxypropionitrile. This process includes (a') reacting acrylonitrile with water at a molar ratio of about 1:0.5 to about 1:20 in the presence of a weak base at a temperature of about 80° C. to about 150° C. and at a pressure of about 1 bar (0.1 MPa) to about 5 bar (0.5 MPa) to form a two-phase organic-aqueous mixture and until a conversion of the acrylonitrile and water to 3-hydroxypropionitrile of about 40% to about 80% is achieved, wherein the organic phase consists essentially of bis(cyanoethyl)ether, 3-hydroxypropionitrile, and unreacted acrylonitrile, and the aqueous phase consists essentially of an aqueous solution of the weak base; (b') cooling the mixture obtained in (a') and neutralizing the weak base by adding a weak acid to the cooled mixture; (c') distilling off the acrylonitrile and the water from the mixture obtained in (b') to obtain a mixture consisting essentially of bis (cyanoethyl)ether, 3-hydroxypropionitrile, and a base formed by the neutralization; (d') heating the mixture obtained in (c') to a temperature of about 120° C. to about 160° C. at a pressure of about 5 mbar (0.5 kPa) to about 500 mbar (50 kPa) in the presence of a base formed by the neutralization in step (b') to obtain a mixture consisting essentially of 3-hydroxypropionitrile and acrylonitrile; and (e') isolating the desired 3-hydroxypropionitrile by fractional distillation from the mixture obtained in (d').

DETAILED DESCRIPTION OF THE INVENTION

The process in accordance with the invention for the production of 3-hydroxypropionitrile is a process that starts from acrylonitrile and water, and includes (a) reacting acrylonitrile with water in a molar ratio of about 1:0.5 to about 1:20 in the presence of a weak base in a temperature range of about 80° C. to about 150° C. and at a pressure of about 1 bar (0.1 MPa) to about 5 bar (0.5 MPa) until a conversion in the range of about 40% to about 80% has been achieved, such that a two-phase organic-aqueous mixture is obtained, wherein the organic phase consists essentially of bis (cyanoethyl)ether, 3-hydroxypropionitrile and unreacted acrylonitrile, and the aqueous phase consists essentially of an aqueous solution of the weak base; (b) cooling the mixture obtained in (a) and separating off its aqueous phase; (c) distilling off the acrylonitrile from the organic phase remaining after (b) in order to obtain a mixture consisting essentially of bis(cyanoethyl)ether and 3-hydroxypropionitrile; (d) subjecting the mixture obtained in (c) to pyrolysis at a temperature range of about 120° C. to about 160° C. and at a reduced pressure of about 5 mbar (0.5 kPa) to about 500 mbar (50 kPa) in the presence of a basic catalyst selected from calcium, magnesium, strontium, titanium, iron and zinc oxides, alkali metal acetates, alkali metal formates, alkali metal and barium carbonates, alkali metal bicarbonates, calcium and copper hydroxides, di- and trisodium phosphates, sodium fluoride, sodium silicate and high boiling trialkylamines in order to obtain a mixture consisting essentially of 3-hydroxypropionitrile and acrylonitrile; and (e) isolating the desired 3-hydroxypropionitrile by fractional distillation from the mixture obtained in (d).

If desired, and even preferably, the aqueous phase separated in process step (b), which contains the majority of the base used in step (a), is conducted back into step (a) of a continuously operated overall process in order to react at step (a) with further acrylonitrile. Likewise, if desired and preferably, the acrylonitrile distilled off in process step (c) and/or in process step (e) is conducted back into step (a) of such process. A process of this kind, which features such recyclization of the basic aqueous phase, as well as of the distilled-off acrylonitrile, is presented schematically as follows:

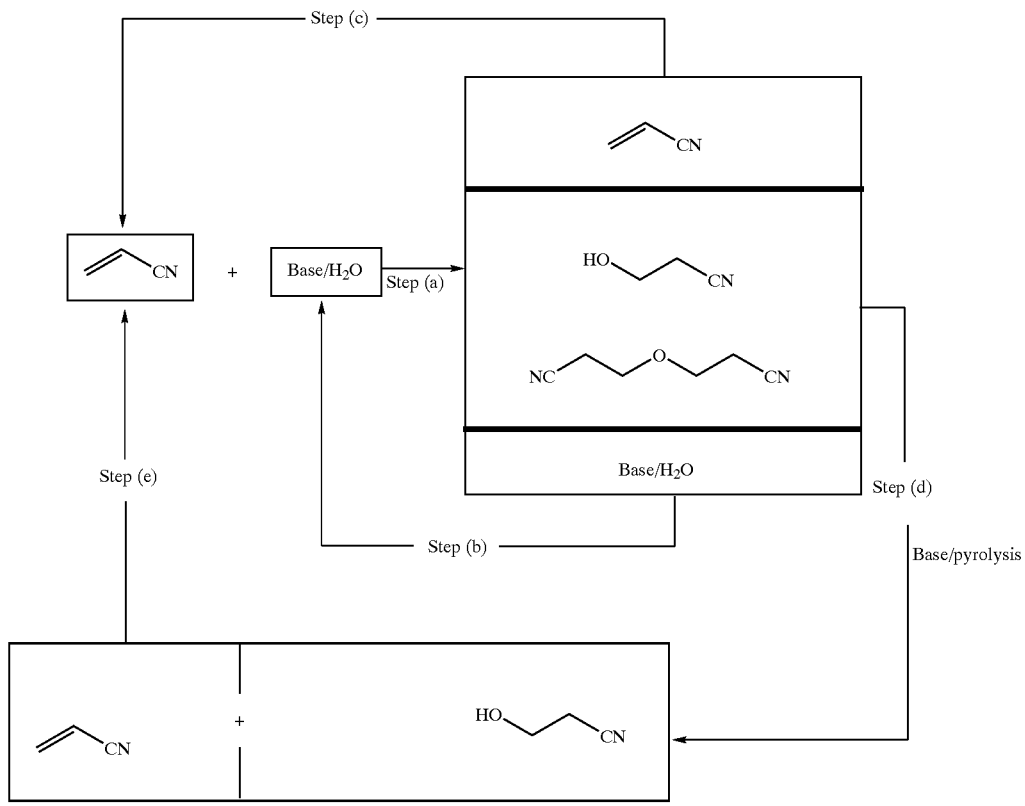

As used herein, the term "weak base" in process step (a) denotes an inorganic or organic base, the $pK_a$ value of which is about 8 to about 12. The inorganic base is preferably an alkali metal carbonate (e.g. sodium or potassium carbonate), an alkali metal bicarbonate, (e.g. sodium or potassium bicarbonate), or a mixture of two or more of these inorganic bases, (e.g. a mixture of sodium carbonate and sodium bicarbonate), and the organic base is preferably a lower trialkylamine or a 4-dialkylaminopyridine. Not only in the case of "lower trialkylamine", but also in the case of "4-dialkylamino-pyridine", the term "alkyl" denotes preferably a $C_{1-6}$-alkyl group. Examples of lower trialkylamines and 4-dialkylamino-pyridines are triethylamine and ethyldiisopropylamine, and 4-dimethylamino-pyridine, respectively. Sodium carbonate, potassium carbonate, a mixture of sodium carbonate and sodium bicarbonate or a mixture of potassium carbonate and potassium bicarbonate is preferably used as the weak base.

The amount of weak base employed is conveniently about 0.1 to about 5 mol. %, preferably about 0.5 to about 2 mol. %, based on the amount of acrylonitrile employed. The reaction of the acrylonitrile with the water is effected in process step (a) generally at a temperature of about 80° C. to about 150° C., preferably at temperatures in the range of about 100° C. to about 130° C., and generally at a pressure of about 1 bar (0.1 MPa) to about 5 bar (0.5 MPa), preferably at about 1 bar (0.1 MPa) to about 3 bar (0.3 MPa).

The acrylonitrile:water molar ratio is generally about 1:0.5 to about 1:20, preferably about 1:3 to about 1:8, particularly about 1:2 to about 1:4.

The expression "wherein the organic phase consists essentially of bis(cyanoethyl)ether, 3-hydroxypropionitrile and unreacted acrylonitrile" occurring in the definition of process step (a) means that the three mentioned components amount to at least 90% by weight of the organic phase. The further expression "the aqueous phase consists essentially of an aqueous solution of the weak base" means that the weak base and the water in which it is dissolved amount to at least 70% by weight of the aqueous phase.

The reaction (condensation) of acrylonitrile with water in the presence of the weak base is conveniently effected on an industrial scale by combining the acrylonitrile with a solution of the base in water at room temperature in an autoclave, and heating the two-phase mixture while stirring. Pressure, which amounts to about 1 to 5 bar (0.1 to 0.5 MPa) depending on the temperature (80° C. to 150° C.), thereby develops in the closed autoclave.

In process step (a), the conversion is intentionally limited to the range of about 40% to about 80%, because a too high conversion leads to excessive production of undesired polymeric byproducts, as well as an increase of undesired acrylamide byproduct. The fact that unreacted acrylonitrile is present in the product is not problematical, because this starting material can be readily recovered in process step (c) and recycled, especially in step (a). Moreover, it is irrelevant whether the ratio of the products bis(cyanoethyl)ether: 3-hydroxypropionitrile in the condensation is large or small because the former product can be readily converted in process step (d) into the desired 3-hydroxypropionitrile, and the latter product is stable under the process conditions in accordance with the invention, especially the pyrolysis conditions of step (d), so that the mixture consisting mainly of the two named products can be subjected directly to pyrolysis.

Limiting the conversion necessitates the control and measurement of conversion, which can be effected conveniently by gas chromatography.

As a rule, process step (a) is completed after about 1 to 2 hours.

The advantage, in the case of step (a), of the overall process in accordance with the invention is, inter alia, the considerable suppression of the formation of undesired polymeric byproducts as well as of the likewise undesired byproduct acrylamide.

In process step (b), the separation of the aqueous phase from the two-phase organic-aqueous mixture obtained in process step (a) is accomplished. Prior to the separation, this mixture is conveniently cooled to a temperature in the range of room temperature to about +10° C., which is effected either without active cooling or by cooling with cold water, for example water at about +5° C. The two phases separate very readily in this temperature range.

The aqueous phase, which contains the major part of the weak base used as the catalyst, can subsequently be separated, which is conveniently effected according to methods known per se.

Preferably, the thus-separated aqueous phase, after possible replenishment with weak base, is subsequently conducted back into step (a) for reaction with additional acrylonitrile, which can also be partially recycled in a second or further cycle of process step (a).

The organic phase, which consists mainly of bis (cyanoethyl)ether, 3-hydroxypropionitrile and unreacted acrylonitrile, remaining after process step (b) has been effected, is then distilled in process step (c) in order to separate the acrylonitrile from the bis(cyanoethyl)ether and 3-hydroxypropionitrile. This is conveniently carried out by distilling off the acrylonitrile, still containing, to some extent, dissolved water, over a distillation column (e.g. a mirrored packed column), at temperatures in the range of about 60° C. to about 100° C. and at a pressure of about 200 mbar (20 kPa) to about 10 mbar (1 kPa). Thereby, the acrylonitrile that is distilled off is collected continuously in a suitable cooled receiver. The mixture obtained in process step (c) is a mixture consisting essentially of bis(cyanoethyl) ether and 3-hydroxypropionitril. The expression "essentially" in this context means that the two mentioned components amount to at least 80% by weight of the mixture.

The thus-separated acrylonitrile, after possible replenishment with additional acrylonitrile is preferably conducted back into step (a) for reaction with water in the presence of a weak base in a second or further cycle of process step (a).

The mixture of (essentially) bis(cyanoethyl)ether and 3-hydroxypropionitrile remaining after process step (c) has been effected is subsequently pyrolyzed in step (d), in which the bis(cyanoethyl)ether is cleaved under basic catalysis into 3-hydroxypropionitrile and acrylonitrile. This reaction occurs without the 3-hydroxypropionitrile, that is likewise present in the mixture itself, reacting. Thus, it is a surprising advantage of the process in accordance with the invention that the desired product remains unchanged under these pyrolysis conditions.

As used herein, the term "alkali metal" in process step (d), signifies in each case lithium, sodium or potassium. When a high boiling trialkylamine is used as the basic catalyst, this refers to a trialkylamine with a boiling point at normal pressure that is higher than about 150° C.; examples are trioctylamine and tridodecylamine.

Calcium oxide, magnesium oxide, the alkali metal acetates, the alkali metal formates, the alkali metal carbonates, barium carbonate, the alkali metal bicarbonates, calcium hydroxide, trisodium phosphate as well as sodium fluoride are preferred among the basic catalysts that can be used. Calcium oxide, sodium acetate and potassium acetate are especially preferred basic catalysts.

The amount of basic catalyst employed, which is based on the total amount of the mixture of bis(cyanoethyl)ether and 3-hydroxypropionitrile obtained in process step (c) and used in process step (d), is conveniently about 0.05 to about 10 weight percent, preferably about 0.1 to about 3 weight percent.

The pyrolysis of process step (d) is effected generally in the temperature range of about 120° C. to about 160° C., preferably at temperatures in the range of about 130° C. to about 150° C., and generally at a reduced pressure of about 5 mbar (0.5 kPa) to about 500 mbar (50 kPa), preferably at about 10 mbar (1 kPa) to about 400 mbar (40 kPa).

A mixture consisting essentially of 3-hydroxypropionitrile and acrylonitrile in the molar ratio of about 1:1 results from the pyrolysis. The duration of the pyrolysis by which such a mixture is obtained depends on the batch size and, as a rule, amounts to at least one hour. Thereby, only very small amounts of acrylamide and polymeric products are produced as byproducts, which is a further advantage of the process in accordance with the invention.

The expression "mixture consisting essentially of 3-hydroxypropionitrile and acrylonitrile" occurring in the previous paragraph and in the definition of process step (d) means that the two mentioned components amount to at least 90% by weight of the mixture.

The pyrolysis can be effected on an industrial scale by continuously distilling off the 3-hydroxypropionitrile and acrylonitrile products formed using a distillation column and collecting them in a cooled receiver simultaneously with pyrolysis. Alternatively, the distillation effected simultaneously with the pyrolysis can be carried out selectively by condensing the two products individually, first the 3-hydroxypropionitrile and then the acrylonitrile, by suitable cooling. In this manner, the fractional distillation of process step (e) is effectively advanced by a combination of process steps (d) and (e). This represents a modification of the process in accordance with the invention.

When the mixture of 3-hydroxypropionitrile and acrylonitrile has been obtained in process step (d), the desired 3-hydroxypropionitrile is isolated by fractional distillation in the last process step, (e). If desired, and preferably, the acrylonitrile which is thereby obtained is conducted back into step (a), and re-used analogously to the situation which is described above in connection with the performance of the earlier step (c).

The fractional distillation in accordance with process step (e) is conveniently effected initially at a bath temperature of about 50° C. to about 120° C. and a pressure of about 180 mbar (18 kPa) to about 10 mbar (1 kPa), whereby the majority of the acrylonitrile is distilled off, and thereafter at a bath temperature of about 120° C. to about 150° C. and a pressure of about 110 mbar (1 kPa) and below, whereby the majority of the desired 3-hydroxypropionitrile [boiling point about 99–102° C./10 mbar (1 kPa)] is obtained. A mirrored packed column can be used, for example, as the distillation column.

In this manner 3-hydroxypropionitrile is obtained in very good purity and in a yield which normally amounts to more than 85%, under optimal conditions more than 90%, based on the amount of the original acrylonitrile [in process step (a)] consumed.

A further aspect of the present invention includes, after achieving the about 40% to 80% conversion in process step (a), neutralizing the weak base by the addition of a weak acid in order to obtain a two-phase organic-aqueous mixture, which instead of the original weak base contains, inter alia, the base formed by the neutralization. This base constitutes the basic catalyst used in the later process step (d), so that the addition of a basic catalyst for process step (d) is avoided.

The overall process in accordance with this aspect of the present invention includes:

(a') reacting acrylonitrile with water at a molar ratio of about 1:0.5 to about 1:20, in the presence of a weak base, at a temperature of about 80° C. to about 150° C. and at a pressure of about 1 bar (0.1 MPa) to about 5 bar (0.5 MPa), until a conversion in the range of about 40% to about 80% has been achieved in order to obtain a two-phase organic-aqueous mixture, the organic phase of which consists essentially of bis(cyanoethyl) ether, 3-hydroxypropionitrile and unreacted acrylonitrile, and the aqueous phase of which consists essentially of an aqueous solution of the weak base; (b') cooling the mixture obtained in (a') and neutralizing the weak base by the addition of a weak acid; (c') distilling off the acrylonitrile and the water from the mixture obtained in (b') in order to obtain a mixture consisting essentially of bis(cyanoethyl)ether, 3-hydroxypropionitrile and the base formed by the neutralization; (d') subjecting the mixture obtained in (c') to pyrolysis at a temperature of about 120° C. to about 160° C. and at a reduced pressure of about 5 mbar (0.5 kPa) to about 500 mbar (50 kPa) in the presence of the already present base, formed by neutralization, in order to obtain a mixture consisting essentially of 3-hydroxypropionitrile and acrylonitrile; and (e') isolating the desired 3-hydroxypropionitrile by, for example, fractional distillation, from the mixture obtained in (d').

Also in this process, if desired, and even preferably, the acrylonitrile distilled off in process step (c') and/or in process step (e') is conducted back into step (a') of a continuously operated overall process in accordance with this aspect of the invention.

The conditions of process steps (a'), (c'), (d') and (e') correspond in general to those conditions which are described above in connection with process steps (a), (c), (d) and (e), respectively. This also applies to process step (c') vis-à-vis process step (c), although in the former step not only acrylonitrile but also water are distilled off, and also to process step (d') vis-à-vis process step (d), although in the former step the base which serves as the basic catalyst is already present in the mixture of bis(cyanoethyl)ether and acrylonitrile after carrying out process step (c'). Furthermore, the expressions "consists essentially of" occurring in the above definition of process step (a'), "consisting essentially of" occurring in the above definition of process step (c'), and "consisting essentially of" occurring in the above definition of process step (d') have the same meanings as given hereinabove in relation to the process steps (a), (c) and (d) of the first mentioned embodiment or aspect of the present invention, i.e. at least 90%, at least 70%, at least 80% and at least 90%, in each case by weight, respectively.

As the weak acid, which is used for the neutralization of the weak base in process step (b'), there is especially used a lower ($C_{1-3}$) carboxylic acid, (e.g. formic acid, acetic acid or propionic acid). For example, when sodium carbonate or sodium bicarbonate is used as the weak base and acetic acid is used as the weak acid, the base sodium acetate is formed by the neutralization. Preferably, a mixture of sodium carbonate and sodium bicarbonate is used as the weak base and acetic acid is used as the weak acid in the process in accordance with this aspect of the present invention.

If desired, the 3-hydroxypropionitrile obtained can be subjected to a hydrogenation to give 3-aminopropanol. Methods known per se can be used for this purpose, for example, using Raney nickel as the catalyst in methanol or ethanol and in the presence of anhydrous ammonia, as described in, for example, Swiss Patent No. 244,837, and J. Chem. Soc. 1946, 94, as well as JP Kokai No. 9963/1989. Ammonia prevents to a large extent the formation of secondary amines. The hydrogenation is conveniently effected at temperatures of about 100° C. and at pressures of about 25 to about 100 bar $H_2$ (about 2.5 to about 10.0 MPa).

The following examples are provided to further illustrate the process of the present invention. These examples are illustrative only and are not intended to limit the scope of the invention in any way.

EXAMPLES

Example 1

Reaction of acrylonitrile with Water and Cleavage of the Resulting bis(cyanoethyl)ether into 3-hydroxypropionitrile and acrylonitrile (a) Sodium carbonate as the Base 159.2 g (3 mol) of acrylonitrile and a solution of 1.6 g (15 mmol, 0.5 mol %) of sodium carbonate in 54 g (3 mol) of deionized water were placed in a stirring autoclave. The autoclave was flushed with argon and closed, and the reaction mixture was heated to 94° C. (internal temperature) within 20 minutes while stirring at 200 rpm. The mixture was then stirred at 94–95° C. for an hour more (jacket temperature 110° C. falling to 98° C.; pressure about 1 bar/0.1 MPa). Then the yellowish two-phase mixture, cooled to about 5–10° C. (internal temperature), was transferred into a separating funnel and the aqueous phase was separated off. This gave 188 g of an organic phase of the following content in area percent (area %) according to gas chromatography (GC):

| | |
|---|---|
| 54% | acrylonitrile |
| 5% | 3-hydroxypropionitrile |
| 38% | bis(cyanoethyl) ether |
| 1% | acrylamide | as well as 26 g of an aqueous phase. The aqueous phase still contained a small amount of the above products. These were disregarded for the yield calculation. However, if desired, this aqueous phase can be used again in process step (a), whereby no product is lost. The excess acrylonitrile containing dissolved water was distilled off from the organic phase (188 g) at 200–10 mbar/20–1 kPa (oil bath: 60° C. to a maximum of 100° C.; b.pt.≦35° C.) over a mirrored 10 cm packed column and conducted into a receiver cooled to −70° C. This gave 80 g of a two-phase distillate, of which the upper phase consisted of 66.1 g of acrylonitrile and the lower phase consisted of 13.9 g of water. Corrected in accordance with the fact that at 20° C. 7.4% acrylonitrile dissolves in water and 3.1% water dissolves in acrylonitrile, this corresponds to 64.8 g (1.22 mol) of acrylonitrile and 15.2 g of water, which corresponds to a conversion of 59.3% of acrylonitrile.

For the fragmentation, 300 mg (about 0.3 wt. %) of sodium acetate were added to the above residue in a sump.

The bath temperature was increased to 130–135° C. and the pressure was reduced, whereby the fragmentation began. The products 3-hydroxypropionitrile, acrylonitrile and a small amount of acrylamide were then distilled off together continuously at 8–9 mbar (0.8–0.9 kPa) over a 10 cm Vigreux column without fractionation into a receiver cooled to −70° C. This gave 103 g of a colorless distillate of the following content in area % according to GC:

| | |
|---|---|
| 60% | acrylonitrile |
| 38% | 3-hydroxypropionitrile |
| 1% | acrylamide |

The residue consisted of 3.8 g of oil.

For the fractional distillation of acrylonitrile and 3-hydroxypropionitrile, the above distillate (103 g) was fractionally distilled under reduced pressure on a mirrored 10 cm packed column. The following two fractions were obtained:

1$^{st}$ Fraction: B.pt.≦35° C./180 to 10 mbar (18 to 1 kPa); bath temperature 50–120° C.; receiver cooled to −70° C.+additional cooling trap (−70° C.); 52.1 g (0.98 mol) yield of acrylonitrile.

2$^{nd}$ Fraction: B.pt. 99–102° C./10 mbar (1 kPa); bath temperature 120–150° C.; 50.2 g (86% corr.) yield of 3-hydroxypropionitrile as a colorless oil; content, in area % according to GC:

| | |
|---|---|
| 96.6% | 3-hydroxypropionitrile |
| 2.6% | acrylamide |

Sodium carbonate+sodium bicarbonate (1:1) as the Base 159.2 g (3 mol) of acrylonitrile and a solution of 6.36 g (60 mmol, 2 mol %) of sodium carbonate and 5.04 g (60 mmol, 2 mol %) of sodium bicarbonate in 90 g (5 mol) of deionized water were placed in a stirring autoclave. The autoclave was flushed with argon and closed. The reaction mixture was heated to 120° C. (external temperature) within 25 minutes while stirring at 200 rpm. The mixture was then stirred at this temperature for 1.5 hours. This gave a maximum internal temperature of 115° C. (pressure: 2.2 bar/0.22 MPa). Then the mixture was cooled to 20° C. and transferred into a 500 ml separating funnel. This gave 189.2 g of a colorless, organic (upper) phase of the following content in area % according to GC:

| | |
|---|---|
| 41% | acrylonitrile |
| 8.5% | 3-hydroxypropionitrile |
| 50% | bis(cyanoethyl) ether |
| 0.5% | acrylamide | and 71.2 g of a light yellowish aqueous (lower) phase. The excess acrylonitrile containing dissolved water was distilled off from the organic phase (189.2 g) at 160–7 mbar/16–0.7 kPa (oil bath: 60° C. to a maximum of 100° C.; b.pt.≦35° C.) over a mirrored 10 cm packed column and conducted into a receiver cooled to −70° C., as well as an additional cooling trap at −70° C. This gave 73.8 g of a two-phase distillate, of which the upper phase consisted of 62.1 g of acrylonitrile and the lower phase consisted of 11.7 g of water. Corrected in accordance with the fact that at 20° C. 7.4% acrylonitrile dissolves in water and 3.1% water dissolves in acrylonitrile, this corresponds to 61.0 g (1.15 mol) of acrylonitrile and 12.8 g of water, which corresponds to a conversion of 60.0% of acrylonitrile.

For the fragmentation, 350 mg (about 0.3 wt. %) of sodium acetate were added to the above residue in a sump [115 g: 65% 3-hydroxypropionitrile, 32% bis(cyanoethyl) ether as well as about 1% acrylamide]. The bath temperature was increased to 130–135° C. and the pressure was reduced, whereby the fragmentation began. The products 3-hydroxypropionitrile, acrylonitrile and a small amount of acrylamide were then distilled off together continuously at 7–8 mbar (0.7–0.8 kPa) over a 10 cm Vigreux column without fractionation into a receiver cooled to −70° C. as well as an additional cooling trap at −70° C. This gave 109 g of a colorless distillate of the following content, in area %, according to GC:

| | |
|---|---|
| 53% | acrylonitrile |
| 46% | 3-hydroxypropionitrile |
| 0.7% | acrylamide |

The residue consisted of 4 g of oil.

For the fractional distillation of acrylonitrile and 3-hydroxypropionitrile, the above distillate (109 g) was fractionally distilled under reduced pressure on a mirrored 10 cm packed column. The following two fractions were obtained:

1$^{st}$ Fraction: B.pt.≦35° C./180 to 10 mbar (18 to 1 kPa); bath temperature 50–120° C.; receiver cooled to −70° C. +additional cooling trap (−70° C.); 50.0 g (0.94 mol) yield of acrylonitrile.

2$^{nd}$ Fraction: B.pt. 99–102° C./10 mbar (1 kPa); 57.5 g (87%, corr.) yield of 3-hydroxypropionitrile as a colorless oil; content in weight percent (wt. %) according to GC:

| | |
|---|---|
| 97.8% | 3-hydroxypropionitrile |
| 1.8% | acrylamide |

The residue consisted of 1.5 g of oil.

(c) Sodium bicarbonate as the Base 159.2 g (3 mol) of acrylonitrile and a solution of 5.04 g (60 mmol, 2 mol %) of sodium bicarbonate in 108 g (6 mol) of deionized water were placed in a stirring autoclave. The autoclave was flushed with argon and closed, and the reaction mixture was heated to 125° C. (external temperature) within 25 minutes while stirring at 200 rpm. The mixture was then stirred at this temperature for 80 minutes. This gave a maximum internal temperature of 120–121° C. (pressure: 3.1 bar/0.31 MPa). Then the colorless two-phase mixture, cooled to 15° C., was transferred into a separating funnel and the aqueous phase was separated off. This gave 173 g of an organic (upper) phase of the following content in area % according to GC:

| | |
|---|---|
| 49.5% | acrylonitrile |
| 18.5% | 3-hydroxypropionitrile |
| 31% | bis(cyanoethyl) ether |
| 0.7% | acrylamide |

In order to obtain the organic products 3-hydroxypropionitrile, bis(cyanoethyl)ether, acrylonitrile and acrylamide present in the aqueous phase, the water was distilled off at 180–8 mbar/18–0.8 kPa over a mirrored 10 cm packed column. This gave 78.3 g of water, that still contained dissolved acrylonitrile (dist. 1) and 19.6 g of a residue (yellowish oil with solid inorganic salt). This was extracted with a total of 125 ml of diethyl ether (once with 50 ml and three times with 25 ml) and the organic phase was concentrated, which gave 14 g of an oily extract.

The aforementioned organic phase (173 g) was then combined with the above extract (14 g). The excess acrylonitrile containing dissolved water was distilled off at 200–10 mbar/20–1 kPa (oil bath: 60° C. to a maximum of 100° C.; b.pt.≦35° C.) over a mirrored 10 cm packed column and collected in a receiver cooled to −70° C. as well an additional cooling trap at −70° C. This gave 107 g of a residue and 79.4 g of a two-phase distillate, which consisted of acrylonitrile and water (dist. 2). The two distillates dist. 1 and dist. 2 (78.3 g+79.4 g =157.7 g) were combined, shaken briefly in a separating funnel at room temperature and separated. This gave an upper phase (64.5 g of acrylonitrile) and a lower phase (93.2 g of water). Corrected in accordance with the fact that at 20° C., 7.4% acrylonitrile dissolves in water and 3.1% water dissolves in acrylonitrile, this corresponds to 68.7 g (1.29 mol) of acrylonitrile and 89 g of water, which corresponds to a conversion of 57% of acrylonitrile.

For the fragmentation, 400 mg (about 0.4 wt. %) of sodium acetate were added to the above distillation residue (107 g). The bath temperature was increased to 130–135° C. and the pressure was reduced, whereby the fragmentation began. The products 3-hydroxypropionitrile, acrylonitrile and a small amount of acrylamide were then distilled off continuously at 8–9 mbar (0.8–0.9 kPa) over a 10 cm Vigreux column without fractionation into a receiver cooled to −70° C. as well as an additional cooling trap at −70° C. This gave 103 g of a colorless distillate of the following content, in area %, according to GC:

| | |
|---|---|
| 46.5% | acrylonitrile |
| 52.5% | 3-hydroxypropionitrile + acrylamide |

The residue consisted of 4 g of oil.

For the fractional distillation of acrylonitrile and 3-hydroxypropionitrile, the above distillate (103 g) was fractionally distilled under reduced pressure on a 10 cm packed column. The following two fractions were obtained:

1$^{st}$ Fraction: B.pt.≦35° C./180 to 10 mbar (18 to 1 kPa); receiver cooled to −70° C.; 41.9 g (0.79 mol) yield of acrylonitrile.

2$^{nd}$ Fraction: B.pt. 99–102° C./10 mbar (1 kPa); 60.1 g (90%, corr.) yield of 3-hydroxypropionitrile as a colorless oil; content in area percent according to GC:

| | |
|---|---|
| 97.5% | 3-hydroxypropionitrile |
| 2.3% | acrylamide |

Example 2

Reaction of acrylonitrile with Water and Cleavage of the Resulting bis(cyanoethyl)ether into 3-hydroxypropionitrile and acrylonitrile Through a Process that Includes the Recycling of acrylonitrile and Water; 6 Cycles Total, of which only the 1$^{st}$ and the 5$^{th}$ Cycle are Exemplified in the Following (a) Sodium carbonate+sodium bicarbonate as the Base
1$^{st}$ Cycle 159.2 g (3 mol) of acrylonitrile and a solution of 6.36 g (60 mmol, 2 mol %) of sodium carbonate and 5.04 g (60 mmol, 2 mol %) of sodium bicarbonate in 90 g (5 mol) of deionized water were placed at room temperature in a 0.5 l stirring autoclave. The autoclave was flushed with argon and closed, and the reaction mixture was stirred at 200 rpm and heated to an internal temperature of 115° C. (varying from 114.5 to 115.1° C.) within 20 minutes. The mixture was then stirred at this temperature for 75 minutes (jacket temperature: 129° C.–117° C.; pressure initially about 3 bar/0.3 MPa, finally 2.8bar/0.28MPa). Subsequently, the mixture was cooled to +6° C. and placed in a separating funnel, the aqueous phase (AP 1) was separated, the organic phase was again placed in the stirring autoclave and stirred with 18 g (1 mol) of water (WW 1) at +5° C. for 15 minutes. After phase separation in the separating funnel, an organic phase (OP 1) and a second aqueous phase (AP 2) were obtained:

| | |
|---|---|
| OP 1 (184.65 g): content according to GC: | 49 g (0.94 mol) of acrylonitrile |
| | 15.9 g (0.22 mol) of 3-hydroxypropionitrile |
| | 94.7 g (0.7 mol) of bis(cyanoethyl) ether |
| | 0.9 g (12 mmol) of acrylamide |
| AP 1 (71.5 g): content according to GC: | 1.0 g (19 mmol) of acrylonitrile |
| | 4.3 g (60 mmol) of 3-hydroxypropionitrile |
| | 3.2 g (25 mmol) of bis(cyanoethyl) ether |
| | 0.2 g (3 mmol) of acrylamide |
| AP 2 (22.3 g): content according to GC: | 0.9 g (16 mmol) of acrylonitrile |
| | 2.1 g (29 mmol) of 3-hydroxypropionitrile |
| | 1.7 g (14 mmol) of bis(cyanoethyl) ether |
| | 0.2 g (3 mmol) of acrylamide |

The excess acrylonitrile containing dissolved water was distilled off from the organic phase (OP 1:184.65 g) at 180–8 mbar/18–0.8 kPa (oil bath: 60° C. to a maximum of 100° C.; b.pt.≦35° C.) over a mirrored 10 cm packed column into a receiver cooled to −70° C. as well as an additional cooling trap at −70° C. This gave 68.3 g of a two-phase distillate (ACN 1+water) of the following composition:

Upper phase: 51.6 g of acrylonitrile
Lower, aqueous phase: 16.7 g of water
Corrected in accordance with the fact that at 20° C., 7.4% acrylonitrile dissolves in water and 3.1% water dissolves in acrylonitrile, this corresponds to 51.2 g of acrylonitrile (ACN 1) and 17.1 g of water (AP 3), which corresponds to a conversion of 67% of acrylonitrile in the 1$^{st}$ cycle.

For the fragmentation, 0.4 g (about 0.4 wt. %) of sodium acetate were added to the above yellowish distillation residue. The bath temperature was increased to 130–135° C. and the pressure was reduced, whereby the fragmentation began. The products 3-hydroxypropionitrile, acrylonitrile and a small amount of acrylamide were then distilled off together continuously at 7–8 mbar/0.7–0.8 kPa over a 10 cm Vigreux column without fractionation into a receiver cooled to −70° C. as well as an additional cooling trap at −70° C. This gave 111 g of a colorless distillate (OP 2) of the following content according to GC:

| | |
|---|---|
| 43.3 g (0.82 mol) | acrylonitrile |
| 61.6 g (0.87 mol) | 3-hydroxypropionitrile |
| 0.8 g (12 mmol) | acrylamide | as well as 3.9 g of a residue.

For the fractional distillation of acrylonitrile and 3-hydroxypropionitrile, the above distillate (111 g) was fractionally distilled under reduced pressure on a mirrored 10 cm packed column:

1st Fraction: B.pt.≦35° C./180 to 10 mbar (18 to 1 kPa); bath temperature 50–120° C. receiver cooled to −70° C.+additional cooling trap (−70° C.); this fraction consisted of 46.1 g (0.87 mol) of acrylonitrile (ACN 2).

2nd Fraction: B.pt. 99–102° C./10 mbar (1 kPa); This fraction consisted of 62 g (67.8%; 0.85 mol) of 3-hydroxypropionitrile as a colorless oil; content according to GC:

| | |
|---|---|
| 98.4% (61 g) | 3-hydroxypropionitrile |
| 1.6% | acrylamide |

The residue weighed 0.7 g.

The yield of 3-hydroxypropionaldehyde in this 1st cycle is low, as expected, since the 3-hydroxypropionitrile and bis(cyanoethyl)ether dissolved in the aqueous phases, AP 1 and AP 2, were not taken into consideration. However, these two phases were used again in the following cycles. Therefore, the yields increased slowly in each of the following cycles and reached the region of 90% (plateau) in the 5th and 6th cycle.

5th Cycle 162 g (3.05 mol) of acrylonitrile consisting of 67 g of acrylonitrile from the 4th cycle (ACN 1), 45 g of acrylonitrile from the 4th cycle (ACN 2) as well as 50 g of additional acrylonitrile (to make up to 162 g) and 111.1 g of aqueous phases (containing regenerated catalyst) consisting of 73.2 g AP 1 (from the 4th cycle),
23.7 g AP 2 (from the 4th cycle) as well as
14.2 g AP 3 (from the 4th cycle)

were placed in a 0.5 l stirring autoclave at room temperature. The autoclave was flushed with a small amount of argon and closed, and the reaction mixture was stirred at 200 rpm and heated to an internal temperature of 115° C. (varying from 114.5 to 115.1° C.) within 20 minutes. The mixture was then stirred at this temperature for 75 minutes (jacket temperature: 129° C.–117° C.; pressure initially about 3 bar/0.3 MPa, finally 2.8 bar/0.28 MPa). Subsequently, the mixture was cooled to +15° C. and placed in a separating funnel, the aqueous phase (AP 1) was separated and the organic phase was again placed in the stirring autoclave and stirred with 18 g (1 mol) of water (WW 1) at +5° C. for 15 minutes. After phase separation in the separating funnel, an organic phase (OP 1 a second aqueous phase (AP 2) were obtained:

| | |
|---|---|
| OP 1 (192.8 g): content according to GC: | 56 g (1.1 mol) of acrylonitrile |
| | 14.6 g (0.21 mol) of 3-hydroxypropionitrile |
| | 87 g (0.70 mol) of bis(cyanoethyl) ether |
| | 1.0 g (13 mmol) of acrylamide |
| AP 1 (71.1 g): content according to GC: | 1.3 g (25 mmol) of acrylonitrile |
| | 4.4 g (61 mmol) of 3-hydroxypropionitrile |
| | 3.0 g (24 mmol) of bis(cyanoethyl) ether |
| | 0.5 g (6 mmol) of acrylamide |
| AP 2 (23.6 g): content according to GC: | 0.9 g (16 mmol) of acrylonitrile |
| | 2.0 g (27 mmol) of 3-hydroxypropionitrile |
| | 1.5 g (11 mmol) of bis(cyanoethyl) ether |
| | 0.3 g (3 mmol) of acrylamide |

The excess acrylonitrile containing dissolved water was distilled off from the of organic phase (OP 1:192.8 g) at 180–8 mbar/18–0.8 kPa (oil bath: 60° C. to a maximum 100° C.; b.pt.≦35° C.) over a mirrored 10 cm packed column into a receiver cooled to −70° C. as well as an additional cooling trap at −70° C. This gave 77.0 g of a two-phase distillate (ACN 1+water) of the following composition:

Upper phase: 63.1 g of acrylonitrile
Lower, aqueous phase: 13.9 g of water

Corrected in accordance with the fact that at 20° C., 7.4% acrylonitrile dissolves in water and 3.1% water dissolves in acrylonitrile, this corresponds to 62 g of acrylonitrile (ACN 1) and 15 g of water (AP 3), which corresponds to a conversion of 62% of acrylonitrile in the 5th cycle.

For the fragmentation, 0.4 g (about 0.4 wt. %) of sodium acetate were added to the above yellowish distillation residue. The bath temperature was increased to 130–135° C. and the pressure was reduced, whereby the fragmentation began. The products 3-hydroxypropionitrile, acrylonitrile and a small amount of acrylamide were then distilled off together continuously at 7–8 mbar/0.7–0.8 kPa over a 10 cm Vigreux column without fractionation into a receiver cooled to −70° C. as well as an additional cooling trap at −70° C. This gave 112.6 g of a colorless distillate (OP 2) of the following content according to GC:

| | |
|---|---|
| 46.5 g (0.82 mol) | acrylonitrile |
| 59.8 g (0.87 mol) | 3-hydroxypropionitrile |
| 0.8 g (12 mmol) | acrylamide | as well as 4.5 g of a residue.

For the fractional distillation of acrylonitrile and 3-hydroxypropionitrile, the above distillate (112.6 g) was fractionally distilled under reduced pressure on a mirrored 10 cm packed column: 1st Fraction: B.pt.≦35° C./180 to 10 mbar (18 to 1 kPa); bath temperature 50–120° C. receiver cooled to −70° C. +additional cooling trap (−70° C.); this fraction consisted of 50.5 g (0.95 mol) of acrylonitrile (ACN 2).

2nd Fraction: B.pt. 99–102° C./10 mbar (1 kPa); this fraction consisted of 60.5 g (0.84 mol, 90%, corr.) of 3-hydroxypropionitrile as a colorless oil; content according to GC:

| | |
|---|---|
| 98.5% | 3-hydroxypropionitrile |
| 1.5% | acrylamide |

The residue weighed 0.9 g.

(b) Sodium bicarbonate as the Base 1st Cycle 159.2 g (3 mol) of acrylonitrile and a solution of 5.04 g (60 mmol, 2 mol %) of sodium bicarbonate in 90 g (5 mol) of deionized water were placed at room temperature in a stirring autoclave. The autoclave was flushed with argon and closed, and the reaction mixture was stirred at 200 rpm and heated to 120° C.±0.5° C. (internal temperature) within 20 minutes. The mixture was then stirred at this temperature for 90 minutes (jacket temperature: 134° C.–122° C.; pressure initially about 3.3 bar/0.33 MPa, finally 2.9 bar/0.29 MPa).

Subsequently, the mixture was cooled to +2° C. and placed in a separating funnel, the aqueous phase (AP 1) was separated off, the organic phase was again placed in the stirring autoclave and stirred with 18 g (1 mol) of water (WW 1) at +5° C. for 15 minutes. After phase separation in the separating funnel an organic phase (OP 1) and a second aqueous phase (AP 2) were obtained:

| OP 1 (166.65 g): content according to GC: | 64.9 g (1.2 mol) of acrylonitrile |
|---|---|
| | 11.4 g (0.16 mol) of 3-hydroxypropionitrile |
| | 74.1 g (0.60 mol) of bis(cyanoethyl) ether |
| | 1.0 g (14 mmol) of acrylamide |
| AP 1 (77.6 g): content according to GC: | 3.1 g (58 mmol) of acrylonitrile |
| | 7.2 g (0.1 mmol) of 3-hydroxypropionitrile |
| | 3.1 g (24 mmol) of bis(cyanoethyl) ether |
| | 1.35 g (19 mmol) of acrylamide |
| AP 2 (23.8 g): content according to GC: | 1.1 g (21 mmol) of acrylonitrile |
| | 2.0 g (28 mmol) of 3-hydroxypropionitrile |
| | 1.0 g (18 mmol) of bis(cyanoethyl) ether |
| | 0.4 g (35 mmol) of acrylamide |

The excess acrylonitrile was distilled off from the organic phase (OP 1:166.5 g) at 180–8 mbar/18–0.8 kPa in the same manner as in the foregoing cycles. This gave 69.7 g of a two-phase distillate (ACN 1+water) of the following composition:
Upper phase: 62 g of acrylonitrile
Lower phase: 7.7 g of water
Corrected in accordance with the fact that at 20° C., 7.4% acrylonitrile dissolves in water and 3.1% water dissolves in acrylonitrile, this corresponds to 60.4 g of acrylonitrile (ACN 1) and 9.3 g of water, which corresponds to a conversion of 62% of acrylonitrile.

For the fragmentation, 0.4 g (about 0.4 wt. %) of potassium acetate were added to the above yellowish distillation residue and fragmentation was carried out as in the foregoing cycles. This gave 86.5 g of a colorless distillate (OP 2) of the following content according to GC:

| 38.3 g (0.72 mol) | acrylonitrile |
|---|---|
| 47.6 g (0.67 mol) | 3-hydroxypropionitrile |
| 0.5 g (7 mmol) | acrylamide | as well as 4.8 g of a residue.

For the fractional distillation of acrylonitrile and 3-hydroxypropionitrile, the above distillate (86.5 g) was now fractionated as in the foregoing cycles:

$1^{st}$ Fraction: B.pt.$\leq$35° C./180 to 10 mbar (18 to 1 kPa); this fraction consisted of 40.3 (0.76 mol) of acrylonitrile (ACN 2).

$2^{nd}$ Fraction: 48.0 g (60%; 0.66 mol, corr.) of 3-hydroxypropionitrile as a colorless oil; content according to GC:

98.2% 3-hydroxypropionitrile as well as 1.6% acrylamide.

The residue weighed 0.6 g.

5 Cycle 160.1 g (3.02 mol) of acrylonitrile consisting of 75.1 g of acrylonitrile (regenerated) from the $4^{th}$ cycle (ACN 1), 40.0 g of acrylonitrile (regenerated) from the $4^{th}$ cycle (ACN 2) as well as 45.0 g of additional acrylonitrile (to make up) and 119.2 g of aqueous phases (AP, containing regenerated catalyst) consisting of 83.7 g AP 1 (from the $4^{th}$ cycle), 24.6 g AP 2 (from the $4^{th}$ cycle) as well as 10.9 g AP 3 (from the $4^{th}$ cycle)

were placed in a 0.5 l stirring autoclave at room temperature. The autoclave was flushed with a small amount of argon and closed, and the reaction mixture was heated to 120° C.±0.5° C. (internal temperature) while stirring at 200 rpm at this temperature for 75 minutes (jacket temperature: 134° C.–122° C.; pressure initially about 3.3 bar/0.33 MPa, finally 2.9 bar/0.29 MPa). Subsequently, the mixture was cooled to +2° C. and placed in a separating funnel, the aqueous phase (AP 1) was separated, the organic phase was again placed in the stirring autoclave and stirred with 18 g (1 mol) of water (WW 1) at +5° C. for 15 minutes. After phase separation in the separating funnel an organic phase (OP 1) and a second aqueous phase (AP 2) were obtained:

| OP 1 (181.6 g): content according to GC: | 79.7 g (1.5 mol) of acrylonitrile |
|---|---|
| | 9.8 g (0.14 mol) of 3-hydroxypropionitrile |
| | 75.2 g (0.61 mol) of bis(cyanoethyl) ether |
| | 1.8 g (25 mmol) of acrylamide |
| AP 1 (87.2 g): content according to GC: | 4.8 g (9 mmol) of acrylonitrile |
| | 6.3 g (88 mmol) of 3-hydroxypropionitrile |
| | 3.2 g (25 mmol) of bis(cyanoethyl) ether |
| | 2.6 g (36 mmol) of acrylamide |
| AP 2 (24.5 g): content according to GC: | 1.3 g (24 mmol) of acrylonitrile |
| | 1.6 g (22 mmol) of 3-hydroxypropionitrile |
| | 1.0 g (7 mmol) of bis(cyanoethyl) ether |
| | 0.7 g (9 mmol) of acrylamide |

The excess acrylonitrile was distilled off from the organic phase (OP 1:181.6 g) at 180–8 mbar/18–0.8 kPa in the same manner as in the foregoing cycles. This gave 90.0 g of a two-phase distillate (ACN 1+water) of the following composition:

Upper phase: 80.8 g of acrylonitrile

Lower phase: 9.2 g of water

Corrected in accordance with the fact that at 20° C., 7.4% acrylonitrile dissolves in water and 3.1% water dissolves in acrylonitrile, this corresponds to 79.0 g of acrylonitrile (ACN 1) and 11.0 g of water (AP 3), which corresponds to a conversion of 51% of acrylonitrile.

For the fragmentation, 0.4 g (about 0.4 wt. %) of potassium acetate were added to the above yellowish distillation residue and fragmentation was carried out as in the foregoing cycles. This gave 88.0 g of a colorless distillate (OP 2) of the following content according to GC:

| | |
|---|---|
| 36.4 g (0.69 mol) | acrylonitrile |
| 47.5 g (0.67 mol) | 3-hydroxypionitrile |
| 2.0 g (24 mmol) | acrylamide | as well as 4.4 g of a residue.

For the fractional distillation of acrylonitrile and 3-hydroxypropionitrile, the above distillate (88.0 g) was fractionated as in the foregoing cycles:

$1^{st}$ Fraction: B.pt.≦35° C./180 to 10 mbar (18 to 1 kPa); this fraction consisted of 38.9 g (0.73 mol) of acrylonitrile (ACN 2).

$2^{nd}$ Fraction: B.pt. 99–102° C./10 mbar (1 kPa); this fraction consisted of 48.0 g (82%, 0.654 mol; corr.) of 3-hydroxypropionitrile as a colorless oil; content according to GC:

96.9% 3-hydroxypropionitrile as well as 2.8% acrylamide.

The residue weighed 0.5 g.

Example 3

Cleavage of bis(cyanoethyl)ether (Experiment Conducted without the Initial Presence of 3-hydroxypropionitrile and acrylonitrile)

a) Cleavage with calcium oxide as the Catalyst 124.2 g (1 mol) of bis(cyanoethyl)ether and 1.24 g (1 wt. %) of calcium oxide (as the cleavage catalyst) were placed in a 500 ml round flask equipped with a magnetic stirrer, fitted 15 cm Vigreux column, Claisen headpiece with descending condenser, and receiver (250 ml round flask) cooled to −70° C. This mixture was heated in an oil bath at 120° C. under reduced pressure (13–10 mbar/1.3–1.0 kPa) while stirring. The pyrolysis began at 110° C. (internal temperature), with the 3-hydroxypropionitrile and acrylonitrile products distilling continuously into the receiver cooled to −70° C. The oil bath temperature was increased to 140° C. towards the end of the reaction. The total reaction time amounted to about 2 hours. There were thus obtained 121.3 g of colorless distillate, which according to GC consisted of 54% acrylonitrile, 45% 3-hydroxypropionitrile as well as 0.4% bis(cyanoethyl)ether. The residue consisted of 4.1 g of an oily suspension (calcium oxide in polymeric material).

The above distillate (121.3 g) was subjected to fractional distillation using a small mirrored packed column about 15 cm long. At an oil bath temperature of 60° C. and a pressure of 200 mbar/20 kPa, there was obtained the $1^{st}$ fraction with a b.pt. of ≦35° C. and consisting of 52.9 g (100% yield) of acrylonitrile (content 100% according to GC) as a colorless liquid. The $2^{nd}$ fraction was obtained with a b.pt. of 103–106° C./13 mbar (1.3 kPa) and consisting of 65.6 g (92%, corr.) of 3-hydroxypropionitrile as a colorless liquid; 99.5% according to GC; $^1$H-NMR (CDCl$_3$): 2.62 (t, J=8 Hz, 2 H), 3.0 (bs, OH), 3.88 (t, J=8 Hz, 2H); IR (film, cm$^{-1}$): 3434 (OH), 2253 (CN).

| Microanalysis | | |
|---|---|---|
| Calc.: C 50.69% | H 7.09% | N 19.71% |
| Found: C 50,85% | H 7.10% | N 19.98% |

The residue consisted of 2.1 g of a pale yellow water-soluble oil.

(b) Cleavage with Sodium Acetate as the Catalyst 124.2 g (1 mol) of bis(cyanoethyl)ether and 1.24 g (1 wt. %) of anhydrous sodium acetate (as the cleavage catalyst) were placed in a 500 ml round flask equipped with a magnetic stirrer, fitted 15 cm Vigreux column, Claisen headpiece with descending condenser, and receiver (250 ml round flask) cooled to −70° C. Fragmentation was carried out as described under (a) at an oil bath temperature of 120–140° C. and at 13–10 mbar/1.3–1.0 kPa. This gave 121.1 g of a colorless distillate, which according to GC consisted of 57% acrylonitrile and 43% 3-hydroxypropionitrile. The residue consisted of 3.0 g of a pale yellow, oily suspension (sodium acetate in polymeric material).

The above distillate (121.1 g) was subjected to a fractional distillation using a small mirrored packed column about 15 cm long. At an oil bath temperature of 60° C. and an initial pressure of 200 mbar/20 kPa, and a final pressure of 20 mbar (2 kPa), there was obtained the $1^{st}$ fraction with a b.pt. of ≦35° C. and consisting of 55.8g (>100%) of acrylonitrile as a colorless liquid. The $2^{nd}$ fraction was obtained with a b.pt. of 103–106° C./13 mbar (1.3 kPa) and consisting of 64.5 g (90.0% corr.) of 3-hydroxypropionitrile as a colorless liquid; content according to GC: 99.0%. The residue consisted of 0.4 g of a colorless oil.

Example 4

Hydrogenation of 3-hydroxypropionitrile to 3-aminopropanol (a) Methanol/ammonia, 75 bar (7.5 MPa) Hydrogen 100 g (1.39 mol, 99% according to GC) of 3-hydroxypropionitrile in 100 ml of methanol were placed in a 500 ml steel stirring autoclave equipped with a gasification stirrer. The solution was saturated with 60 g of gaseous ammonia. Subsequently, 10 g of Raney nickel were added and, after flushing with nitrogen, the autoclave was closed. The autoclave was pressurized to 22 bar (2.2 MPa) with hydrogen and the mixture was heated to 100° C. within one hour. The mixture was hydrogenated further at 100° C. while increasing the hydrogen pressure to 75 bar (7.5 MPa). After cooling the contents of the autoclave were filtered over 25 g of Speedex-Dicalite and rinsed with methanol. The major part of the methanol was removed by distillation at about 25 mbar (2.5 kPa)/40° C. This gave 108 g of a blue colored residue, which still contained some methanol. Distillation over a 10 cm packed column at 2–3 mbar (0.2–0.3 kPa) gave 95 g (86.5%, corr.) of 3-aminopropanol as a colorless distillate, b.pt. 59–63° C./2–3 mbar (0.2–0.3 kPa); content according to GC: 95.3%; $^1$H-NMR (CDCl$_3$, 400 MHz): 1.68 (quint., J=6 Hz, 2H), 2.97, 2.3 (b, 3H), 2.97 (t, J=7 Hz, 2H), 3.81 (t, J=6 Hz, 2H); IR (film, cm$^1$): 3350 (b, OH, NH$_2$), 1050 (J).

| Microanalysis | | |
|---|---|---|
| Calc.: C 47.97% | H 12.08% | N 18.65% |
| Found: C 47.77% | H 11.89% | N 18.52% |
| (H$_2$O: 0.61%) | | |

The residue weighed 6.5 g.

(b) Methanol/ammonia, 50 bar (50 MPa) Hydrogen 100 g (1.39 mol; 99% according to GC) of 3-hydroxypropionitrile were placed in 100 ml of methanol.

The solution was saturated at 15–20° C. with 25 g of gaseous ammonia and thereafter transferred into a 500 ml steel stirring autoclave equipped with a gasification stirrer. Then 10 g of Raney nickel were added and, after flushing with nitrogen, the autoclave was closed. The autoclave was pressurized to 22 bar (2.2 MPa) with hydrogen and the mixture was heated to 100° C. within one hour. The hydrogen pressure was increased to 50 bar (5.0 MPa) and the 3-hydroxypropionitrile was hydrogenated for a further 5 hours at 100° C. After cooling the mixture was filtered over 25 g of Speedex-Dicalite, rinsed with methanol and the major part of the methanol was removed under reduced pressure. This gave 104 g of a blue-green residue. Distillation over a 10 cm packed column at 2–3 mbar/ 0.2–0.3 kPa gave 89.7 g (81%, corr.) of 3-aminopropanol as a colorless oil, b.pt. 60.2–64° C./2–3 mbar (0.2–0.3 kPa). The oil crystallized at about 0° C. Content according to GC: 93.6%; $^1$H-NMR (CDCl$_3$, 400 MHz): 1.68 (quint., J=6 Hz, 2H), 2.27 (b, OH, NH$_2$, 3H), 2.97 (t, J=7Hz, 2H), 3.81 (t, J=6 Hz, 2H).

| Microanalysis | | |
|---|---|---|
| Calc.: C 47.97% | H 12.08% | N 18.65% |
| Found: C 48.43% | H 11.94% | N 18.76% |
| (H$_2$O: 1.53%) | | |

(c) Ammonia, 50 bar (5.0 MPa) Hydrogen 200 g (2.78 mol, 99% according to GC) of 3-hydroxypropionitrile were placed in a 500 ml steel stirring autoclave equipped with a gasification stirrer, 20 g of Raney nickel were added and, after closing the autoclave, 60 g of ammonia were compressed in from a steel cylinder. After the additional compression of 22 bar (2.2 mbar) of hydrogen, the mixture was heated to 100° C., the hydrogen pressure was increased to 50 bar (5.0 MPa) and the mixture was hydrogenated at this temperature for 4 hours. After cooling the ammonia was evaporated off and the residue was filtered with methanol over 25 g of Speedex-Dicalite, rinsed with methanol and the major part of the methanol was removed under reduced pressure. This gave 211 g of a green-blue, oily residue, which was distilled over a 10 cm packed column at 2–3 mbar/0.2–0.3 kPa. In this manner there were obtained 182.2 g (83%, corr.) of 3-aminopropanol as a colorless oil, b.pt. 60–62.3° C./2–3 mbar (0.2–0.3 kPa). The oil crystallized at about 0° C. Content according to GC: 95.1%. $^1$H-NMR (CDCl$_3$, 400 MHz): identical with the spectrum given previously under (b).

| Microanalysis | | |
|---|---|---|
| Calc.: C 47.97% | H 12.08% | N 18.65% |
| Found: C 48.14% | H 11.97% | N 18.87% |
| (H$_2$O: 1.17%) | | |

(d) Isopropanol 50 bar (5.0 MPa) Hydrogen 100 g (1.39 mol, 99% according to GC) of 3-hydroxypropionitrile were placed in 100 g of isopropanol in a 500 ml steel stirring autoclave equipped with a gasification stirrer. 10 g of Raney nickel were added thereto while gassing with nitrogen and the autoclave was closed. The mixture was hydrogenated for 7 hours at 100° C. and 50 bar/5.0 MPa hydrogen pressure. Working up of the reaction, as in the foregoing variants (a)–(c), gave 112 g of a green-blue, oily residue, which was distilled, as usual, at 2–3 mbar/0.2–0.3 kPa. In this manner there were obtained 71.7 g (57.6%, corr.) of 3-aminopropanol as a colorless oil, b.pt. 61.3–64.7° C./2–3 mbar (0.2–0.3 kPa). Content according to GC: 84.1%. $^1$H-NMR (CDCl$_3$, 400 MHz): identical with the spectrum given previously under (b).

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for producing 3-hydroxypropionitrile comprising:
   (a) reacting acrylonitrile with water at a molar ratio of about 1:0.5 to about 1:20 in the presence of a weak base at a temperature of about 80° C. to about 150° C. and at a pressure of about 1 bar (0.1 MPa) to about 5 bar (0.5 MPa) to form a two-phase organic-aqueous mixture and until a conversion of the acrylonitrile and water to 3-hydroxypropionitrile of about 40% to about 80% is achieved, wherein the organic phase consists essentially of bis(cyanoethyl)ether, 3-hydroxypropionitrile and unreacted acrylonitrile, and the aqueous phase consists essentially of an aqueous solution of the weak base;
   (b) cooling the mixture obtained in (a) and separating the aqueous phase from the organic phase;
   (c) distilling off the acrylonitrile from the organic phase remaining after (b) to obtain a mixture consisting essentially of bis(cyanoethyl)ether and 3-hydroxypropionitrile;
   (d) heating the mixture obtained in (c) to a temperature of about 120° C. to about 160° C. at a pressure of about 5 mbar (0.5 kPa) to about 500 mbar (50 kPa) in the presence of a basic catalyst selected from the group consisting of calcium, magnesium, strontium, titanium, iron and zinc oxides, alkali metal acetates, alkali metal formates, alkali metal and barium carbonates, alkali metal bicarbonates, calcium and copper hydroxides, di- and trisodium phosphates, sodium fluoride, sodium silicate and high boiling trialkylamines, to form a mixture consisting essentially of 3-hydroxypropionitrile and acrylonitrile; and
   (e) isolating the 3-hydroxypropionitrile by fractional distillation from the mixture obtained in (d).

2. A process according to claim 1 further comprising returning the aqueous phase separated off in process step (b) back to process step (a) for further reaction with additional acrylonitrile.

3. A process according to claim 1 wherein the acrylonitrile distilled off or remaining behind in process step (c) and/or (e) is returned back to process step (a) for further reaction with additional water in the presence of a weak base.

4. A process according to claim 1 wherein the weak base in process step (a) is selected from the group consisting of an alkali metal carbonate, an alkali metal bicarbonate, and a weak organic base.

5. A process according to claim 4 wherein the weak base is a mixture of two or more inorganic bases.

6. A process according to claim 4 wherein the weak base is selected from the group consisting of sodium carbonate, potassium carbonate, a mixture of sodium carbonate and sodium bicarbonate, and a mixture of potassium carbonate and potassium bicarbonate.

7. A process according to claim 1 wherein the amount of the weak base employed is about 0.1 to about 5 mol %, based on the amount of acrylonitrile.

8. A process according to claim 7 wherein amount of the weak base employed is about 0.5 to about 2 mol %, based on the amount of acrylonitrile.

9. A process according to claim 1 wherein the acrylonitrile:water molar ratio in process step (a) is about 1:3 to about 1:8.

10. A process according to claim 9 wherein the acrylonitrile:water molar ratio in process step (a) is about 1:2 to about 1:4.

11. A process according to claim 1 wherein the reaction of the acrylonitrile with the water in process step (a) is effected at a temperature of about 100° C. to about 130° C., and at a pressure of about 1 bar (0.1 MPa) to about 3 bar (0.3 MPa).

12. A process according to claim 1 wherein the basic catalyst in step (d) is selected from the group consisting of calcium oxide, magnesium oxide, sodium acetate, potassium acetate, sodium formate, potassium formate, sodium carbonate, potassium carbonate, barium carbonate, sodium bicarbonate, potassium bicarbonate, calcium hydroxide, trisodium phosphate, and sodium fluoride.

13. A process according to claim 12 wherein the basic catalyst in step (d) is selected from the group consisting of calcium oxide, sodium acetate, and potassium acetate.

14. A process according to claim 1 wherein the amount of the basic catalyst in step (d) is about 0.05 to about 10 weight percent based on the total amount of the mixture of bis(cyanoethyl)ether and 3-hydroxypropionitrile obtained in process step (c) and employed in process step (d).

15. A process according to claim 14 wherein the amount of the basic catalyst is about 0.1 to about 3 weight percent.

16. A process according to claim 1 wherein the heating step (d) is effected at temperatures of about 130° C. to about 150° C. and at a pressure of about 10 mbar (1 kPa) to about 400 mbar (40 kPa).

17. A process for the production of 3-hydroxypropionitrile comprising:

(a') reacting acrylonitrile with water at a molar ratio of about 1:0.5 to about 1:20 in the presence of a weak base at a temperature of about 80° C. to about 150° C. and at a pressure of about 1 bar (0.1 MPa) to about 5 bar (0.5 MPa) to form a two-phase organic-aqueous mixture and until a conversion of the acrylonitrile and water to 3-hydroxypropionitrile of about 40% to about 80% is achieved, wherein the organic phase consists essentially of bis(cyanoethyl)ether, 3-hydroxypropionitrile and unreacted acrylonitrile, and the aqueous phase consists essentially of an aqueous solution of the weak base;

(b') cooling the mixture obtained in (a'), and neutralizing the weak base by adding a weak acid to the cooled mixture;

(c') distilling off the acrylonitrile and the water from the mixture obtained in (b') to obtain a mixture consisting essentially of bis(cyanoethyl)ether, 3-hydroxypropionitrile, and the base formed by the neutralization;

(d') heating the mixture obtained in (c') to a temperature of about 120° C. to about 160° C. at a pressure of about 5 mbar (0.5 kPa) to about 500 mbar (50 kPa) in the presence of a base formed by the neutralization in step (b') to obtain a mixture consisting essentially of 3-hydroxypropionitrile and acrylonitrile; and (e') isolating the desired 3-hydroxypropionitrile by fractional distillation from the mixture obtained in (d').

* * * * *

UNITED STATES PATENT AND TRADEMARK OFFICE
CERTIFICATE OF CORRECTION

PATENT NO.   : 6,462,219 B2
DATED        : October 8, 2002
INVENTOR(S)  : Bruno Burdet et al.

It is certified that error appears in the above-identified patent and that said Letters Patent is hereby corrected as shown below:

<u>Title page,</u>
Item [75], Inventors, insert the city of residence of "Karin Riegl" as
-- Bad Krozingen (DE) --; and in the city of residence of "Johann Riegl," please change "Bad-Krozingen (DE) to -- Bad Krozingen (DE) --;

<u>Column 22,</u>
Lines 22 and 30, please insert a space between "bis(cyanoethyl)" and "ether";

<u>Column 23,</u>
Line 1, after "wherein" please insert -- the --;
Line 5, please change "13" to -- 1:3 --;
Line 27, please insert a space between "(cyanoethyl)" and "ether";

<u>Column 24,</u>
Line 3, please change "(a′)" to -- (a) --;
Line 11, please insert a space between "bis(cyanoethyl)" and "ether";
Line 16, please change "(b′)" to -- (b) --, and "(a′)" to -- (a) --;
Line 19, please change "(c′)" to -- (c) --;
Line 21, please insert a space in between "bis(cyanoethyl)" and "ether";
Line 25, please change "(d′)" to -- (d) --, and "(c′)" to -- (c) --;
Line 31, please change "(e′)" to -- (e) --;
Line 32, please change "(d′)" to -- (d) --.

Signed and Sealed this

Twenty-sixth Day of August, 2003

JAMES E. ROGAN
*Director of the United States Patent and Trademark Office*